US006970287B1

(12) United States Patent
Watkins et al.

(10) Patent No.: US 6,970,287 B1
(45) Date of Patent: Nov. 29, 2005

(54) CONFOCAL 3D INSPECTION SYSTEM AND PROCESS

(75) Inventors: Cory Watkins, Chanhassen, MN (US); David Vaughn, Edina, MN (US)

(73) Assignee: August Technology Corp., Bloomington, MN (US)

( * ) Notice: Subject to any disclaimer, the term of this patent is extended or adjusted under 35 U.S.C. 154(b) by 38 days.

(21) Appl. No.: 10/196,735

(22) Filed: Jul. 16, 2002

Related U.S. Application Data

(60) Provisional application No. 60/305,823, filed on Jul. 16, 2001.

(51) Int. Cl.[7] .......................... G02B 21/00; G01N 21/00
(52) U.S. Cl. .................. 359/368; 359/234; 356/237.4
(58) Field of Search ................ 359/368–390, 359/227–236; 250/201.3–201.7, 216, 561, 250/234–236; 356/375–376, 429, 237.1–9

(56) References Cited

U.S. PATENT DOCUMENTS

| | | | | |
|---|---|---|---|---|
| 3,926,500 A | * | 12/1975 | Frosch et al. ............... 359/235 |
| 4,719,341 A | | 1/1988 | Hoogenboom .............. 250/201 |
| RE32,660 E | | 5/1988 | Lindow et al. .............. 250/201 |
| 4,802,748 A | * | 2/1989 | McCarthy et al. .......... 359/368 |
| 4,806,004 A | * | 2/1989 | Wayland ..................... 359/389 |
| 4,930,896 A | | 6/1990 | Horikawa .................... 356/376 |
| 4,965,442 A | | 10/1990 | Girod et al. ............. 250/201.7 |
| 5,067,805 A | * | 11/1991 | Corle et al. ................. 359/235 |
| 5,072,128 A | | 12/1991 | Hayano et al. ............. 250/572 |
| 5,073,018 A | * | 12/1991 | Kino et al. .................. 359/368 |
| 5,083,220 A | * | 1/1992 | Hill ............................. 359/234 |
| 5,248,876 A | * | 9/1993 | Kerstens et al. ....... 250/559.05 |
| 5,329,358 A | | 7/1994 | Horijon ....................... 356/375 |
| 5,386,317 A | | 1/1995 | Corle et al. ................. 359/386 |
| 5,428,475 A | * | 6/1995 | Tanaami et al. ............ 359/368 |
| 5,448,359 A | | 9/1995 | Schick et al. ............... 356/375 |
| 5,594,242 A | | 1/1997 | Konishi et al. ............. 250/234 |
| 5,633,751 A | * | 5/1997 | Tanaami et al. ............ 359/368 |
| 5,696,591 A | | 12/1997 | Bilhorn et al. ............. 356/429 |
| 5,734,497 A | * | 3/1998 | Yano et al. ................. 359/368 |
| 5,737,084 A | | 4/1998 | Ishihara ...................... 356/376 |
| 5,991,040 A | | 11/1999 | Doemens et al. .......... 356/375 |
| 6,108,090 A | | 8/2000 | Ishihara ...................... 356/376 |
| 6,224,276 B1 | | 5/2001 | Funayama et al. ....... 400/227.1 |
| 6,288,382 B1 | | 9/2001 | Ishihara ................... 250/201.3 |
| 6,426,835 B1 | | 7/2002 | Endo et al. ................. 359/388 |
| 6,773,935 B2 | * | 8/2004 | Watkins et al. ............... 438/14 |

FOREIGN PATENT DOCUMENTS

| | | | | |
|---|---|---|---|---|
| EP | 0 615607 | | 11/1992 | |
| WO | WO 92/14118 | | 8/1992 | |
| WO | WO 93/11403 | | 6/1993 | |
| WO | WO 99/63381 | * | 12/1999 | ............... 359/368 |
| WO | WO 01/37025 | * | 5/2001 | ............... 359/368 |
| WO | WO 03/008940 | | 1/2003 | |

* cited by examiner

*Primary Examiner*—Thong Q Nguyen
(74) *Attorney, Agent, or Firm*—Dicke, Billig & Czaja, PLLC

(57) ABSTRACT

An inspection device comprises a light source, a pellicle beamsplitter for receiving light from the light source and for redirecting the light, and an aperture array for receiving light from the pellicle beamsplitter. The aperture array is a two dimensional array of pinholes having an x axis and a y axis ninety degrees apart, wherein the distance between pinholes in the x direction is greater than the distance between pinholes in the y direction. The inspection device further comprises an imaging system comprising an object imager including a plurality of lenses, a camera reimager including a plurality of lenses, and a camera for acquiring an image.

12 Claims, 2 Drawing Sheets

CONFOCAL 3D INSPECTION SYSTEM AND PROCESS

CROSS REFERENCE TO RELATED APPLICATIONS

This application claims priority to the following provisional patent application filed on Jul. 16, 2001: U.S. Ser. No. 60/305,823.

BACKGROUND OF THE INVENTION

1. Technical Field

The present invention relates to a system, and process for use thereof, for inspecting wafers and other semiconductor or microelectronic substrates, and specifically for inspecting three dimensional (3D) surfaces or features thereon such as bumps. Specifically, the present invention relates to a confocal optical system for inspecting bumps and other 3D features on wafers or like substrates, and a process of using such system.

2. Background Information

Over the past several decades, the microelectronics and semiconductor has exponentially grown in use and popularity. Microelectronics and semiconductors have in effect revolutionized society by introducing computers, electronic advances, and generally revolutionizing many previously difficult, expensive and/or time consuming mechanical processes into simplistic and quick electronic processes. This boom has been fueled by an insatiable desire by business and individuals for computers and electronics, and more particularly, faster, more advanced computers and electronics whether it be on an assembly line, on test equipment in a lab, on the personal computer at one's desk, or in the home via electronics and toys.

The manufacturers of microelectronics and semiconductors have made vast improvements in end product quality, speed and performance as well as in manufacturing process quality, speed and performance. However, there continues to be demand for faster, more reliable and higher performing semiconductors.

One process that has evolved over the past decade plus is the microelectronic and semiconductor inspection process. The merit in inspecting microelectronics and semiconductors throughout the manufacturing process is obvious in that bad wafers may be removed at the various steps rather than processed to completion only to find out a defect exists either by end inspection or by failure during use. In the beginning, wafers and like substrates were manually inspected such as by humans using microscopes. As the process has evolved, many different systems, devices, apparatus, and methods have been developed to automate this process, such as the method developed by August Technology and disclosed in U.S. patent application Ser. No. 09/352,564, now U.S. Pat. No. 6,324,298. Many of these automated inspection systems, devices, apparatus, and methods focus on two dimensional inspection, that is inspection of wafers or substrates that are substantially or mostly planar in nature.

One rapidly growing area in the semiconductor industry is the use of bumps or other three dimensional (3D) features that protrude outward from the wafer or substrate. The manufacturers, processors, and users of such wafers or like substrates having bumps or other three dimensional desire to inspect these wafers or like substrates in the same or similar manner to the two dimensional substrates. However, many obstacles exist as the significant height of bumps or the like causes focusing problems, shadowing problems, and just general depth perception problems. Many of the current systems, devices, apparatus, and methods are either completely insufficient to handle these problems or cannot satisfy the speed, accuracy, and other requirements.

SUMMARY OF THE INVENTION

The inspecting of semiconductors or like substrates, and specifically the inspection of three dimensional surfaces or features, such as bumps, is accomplished by the present invention, which is a confocal sensor with a given depth response functioning using the principle of eliminating out of focus light thereby resulting in the sensor producing a signal only when the surface being inspected is in a narrow focal range. The result is an accurate height determination for a given point or area being inspected such that the accumulation of a plurality of height determinations from use of the confocal sensor system across a large surface allows the user to determine the topography thereof.

In sum, this system and process creates multiple parallel confocal optical paths whereby the out of focus light is eliminated by placing an aperture at a plane which is a conjugate focal plane to the surface of the sample. The result is that the sensor produces a signal only when the sample surface is in a narrow focal range.

BRIEF DESCRIPTION OF THE DRAWINGS

Preferred embodiment of the invention, illustrative of the best mode in which applicant has contemplated applying the principles, are set forth in the following description and are shown in the drawings and are particularly and distinctly pointed out and set forth in the appended claims.

Similar numerals refer to similar parts throughout the drawings.

DESCRIPTION OF THE PREFERRED EMBODIMENT

Figure 1:
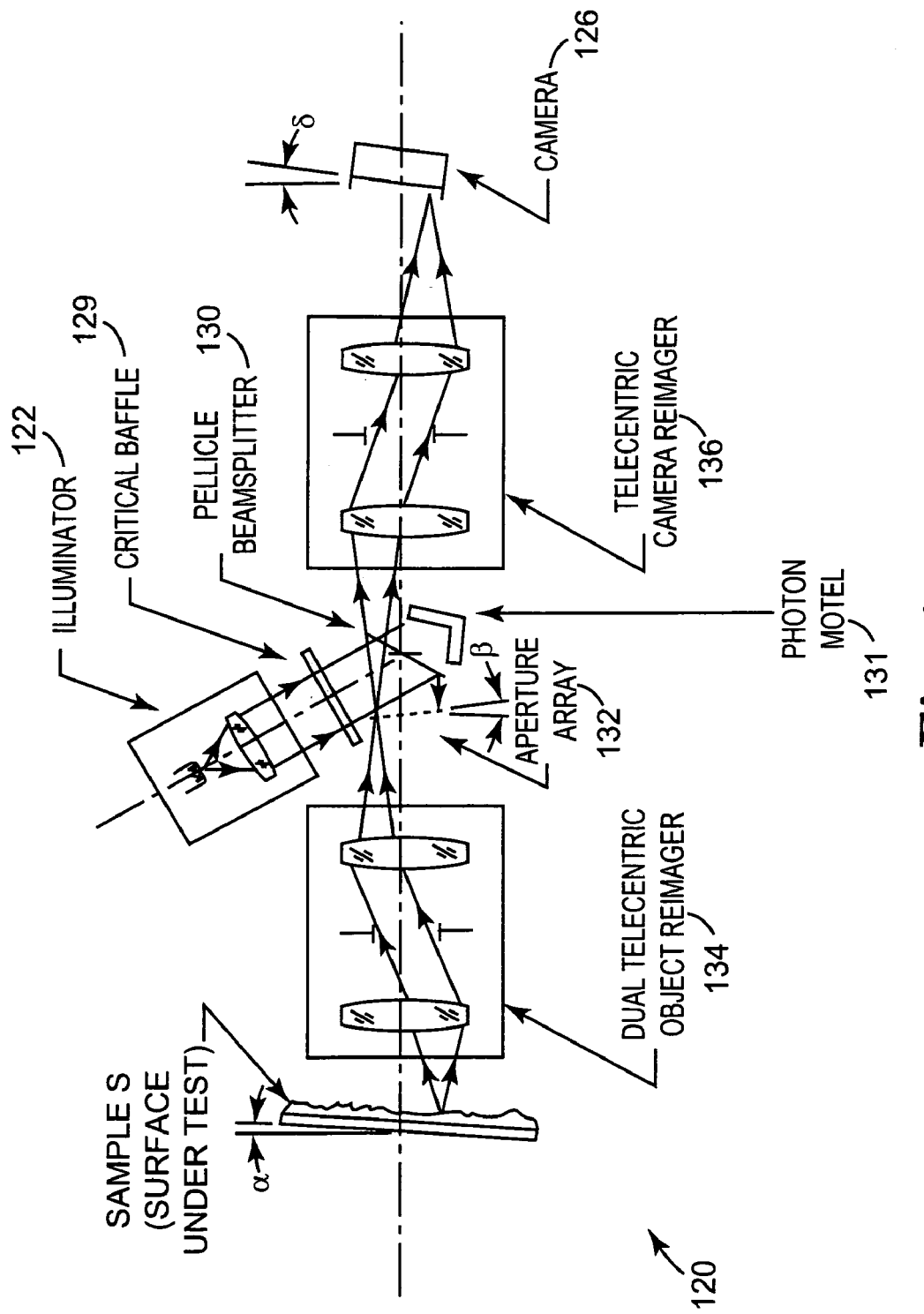
FIG. 1 is a drawing of one embodiment of the present invention.

The three dimensional (3D) inspection system of the present invention is indicated generally at 120 as is best shown overall in FIG. 1 and is used in one environment to view, inspect, or otherwise optically measure three dimensional features or surfaces. One example is the measurement of bumps on wafers or like substrates. The 3D inspection system includes a light source 122, an optical subsystem, and a camera 126. The optical subsystem includes an intermediate focal assembly and a pair of imager or reimagers. The intermediate focal assembly in one embodiment includes an optional critical baffle 129, a beamsplitter 130, a photon motel 131, and an array mount including an aperture array 132, while the imager/reimagers in one embodiment include an object imager 134, and a camera reimager 136.

The light source 122 is any source of light that provides sufficient light to illuminate the sample S, and the light source may be positioned in any position so long as it provides the necessary light to sample S to be viewed, inspected or otherwise optically observed. Examples of the light source include, but are not limited to white light sources such as halogen or arc lights, lasers, light emitting diodes (LEDs) including white LEDs or any of the various colored LEDs, fluorescent lights, or any other type of light source.

In the preferred embodiment, the light source 122 is an incoherent light source, preferably of an incandescent type, that includes a filament, a condenser lens and a heat absorbing glass. In one embodiment, which is most preferred and is shown in the Figures, the light source is an incoherent, optimally baffled, lamp. It is also preferred in certain embodiments that the light source is spatially uniform and of a quasi-telecentric or preferably telecentric design. The system also needs bright light which is typically provided by a broadband or broad-spectrum style light source. It is also very desirable to define the light source as one of a matched numerical aperture design with the object imager to reduce stray light and improve efficiency.

One style of incoherent light source is an incandescent lamp such as a halogen lamp such as a 12 volt, 100 watt quartz-style halogen lamp with a color temperature in the 3000–3500 Kelvin range. Halogen provides a very consistent, stable light output that is broadband or over many wavelengths and is cost effective and readily manufacturable. It is highly preferred that the light source is incoherent to avoid or reduce spatial non uniformity and/or speckle.

The light source is of a Köhler design such as a simple or reimaged Köhler design, and most preferably a reimaged Köhler design which includes additional lenses beyond the condenser lens, which effectively matches the telecentric properties of the optical subsystem thereby matching the numerical aperture and field properties needed by the system 120 to produce accurate height measurements of bumps on the surface of the sample S. One of the embodiments to create such a Köhler or reimaged Köhler system uses an aspheric condenser lens.

One of the advantages of our Köhler or reimaged Köhler design is that every field position or spot in our field "sees" all of the filament so the system has a very uniform irradiance.

The spatial extent of the source coupled with the numerical aperture of the condenser lens plus the focal length and the conjugate provides a combination of field of view and numerical aperture that is optimized. The system optimizes the $A\Omega$ where the A is the size of the area of the field and $\Omega$ is the solid angle of the cone of light. This provides a very uniform field. The Köhler illumination design (1) maps pupil of light source onto spatial extension of aperture array, and (2) maps spatial extension of filament in light source into numerical aperture or angle space of reimaging system. The reimaged Köhler design differs from a standard Köhler design in two ways: (1) reimaged Köhler designs have a filament that is reimaged to a circular aperture that very precisely defines a constant numerical aperture over an entire field, and (2) in between the filament and the sample there is a focal plane that is conjugated to our aperture array, and at that focal plane the light is baffled and masked so that light outside of the desired range at the aperture array never enters the system. One baffle defines the numerical aperture and another baffle limits the light that passes through to only light within the desired field of view.

In one embodiment, the filament length, width and packing density are optimized. The filament length, width and packing density are adjustable to scale the system to inspect significantly larger or smaller bumps or the like.

In one embodiment, the light source is also broadband which provides significant light to the system, and avoids laser-based system speckle problems. The broadband concept provides light across many wavelengths versus a single or small range of wavelengths. This broadband is provided by mercury-type, incandescent-type or other broadband light sources.

In the telecentric environment of one of the embodiments, it is optional to provide an intermediate numerical aperture stop and intermediate field stop that provides improved stray light elimination.

In the quasi-telecentric environment of one of the embodiments, the system has an illuminator interface in the light path adjacent to the illuminator or light source 122. This illuminator interface provides optimal baffling to better match the illuminator cone of light with the field of view cone of light, i.e., in effect improving the quasi-telecentricity to as close as possible to complete telecentricity. In various embodiments, from one to multiple baffles are provided in front of the illuminator, and optimally sized and shaped. These baffles are basically windows that are sized and shaped to allow desirable light through while eliminating stray, peripheral or other undesirable light. This provides the optimal signal to noise ratio. Additionally in a non-preferred embodiment, an optical filter may be used in conjunction with baffling within the illuminator interface. This removes unwanted wavelengths of light.

A thermal barrier may optionally also be provided to reduce the heat transfer of the light from the light source to other components of the system. This reduces or eliminates thermal expansion which causes distortions. The thermal barrier is preferably placed between the lens and the baffle.

This light source provides sufficient energy to illuminate the sample S. The light emitted from the light source 122 is directed into the optical subsystem. Specifically the light is directed toward beamsplitter 130.

In more detail and in the embodiment shown in the Figures, the optical subsystem includes the intermediate focal assembly including the critical baffle 129, beamsplitter 130, photon motel 131, and array mount with aperture array 132, and the system further includes object imager 134, and camera reimager 136.

Critical baffle 129 is an optional additional baffle that is positioned as close as possible to an intermediate focal surface as possible. The critical baffle is positioned in between the light source and the beamsplitter and is preferably as close as possible to the beamsplitter. The critical baffle reduces stray light entering the intermediate focal assembly as well as removing stray reflections off of the beamsplitter.

Beamsplitter 130 in the embodiment shown is a pellicle beamsplitter. A pellicle beamsplitter has several advantages since it is achromatic, has very low polarization effects, and less variation with angle and color issues, and more uniformly provides light even after beam splitting effects than a polarized beamsplitter. A pellicle beamsplitter also allows for an optical system that does not need a ¼ waveplate.

Another important feature is the design, setup, alignment and configuration of the light source 122, pellicle beam splitter 130 and the aperture array 132 as is shown in the FIG. 1. The light or illumination source 122 provides reflected light to the beamsplitter whereby some of this light passes through the beamsplitter and emanates out of the entire system and is lost, a small amount may be lost within the beamsplitter, and the remaining light is reflected toward the aperture array. In one embodiment as is shown in the Figures, the camera is axial with the imager/reimagers while the light source is not and uses the beamsplitter to introduce the light into the axis defined between the imager/reimagers 134 and 136 and the camera. This design maintains a good transmitted wave front through a pellicle beamsplitter, i.e., the imaging performance is preserved between the imager/reimagers through the array and beamsplitter. The reason for the maintaining of this good transmitted wave front is the combination of the axial camera and reimager design coupled with a pellicle beamsplitter as defined below rather than a polarizing beamsplitter since the pellicle beamsplitter have good transmitting wave fronts in comparison to reflective wave fronts versus the polarizing beamsplitter which has good reflective wave fronts in comparison to its transmitted wave front.

The beamsplitter 130 is pellicle and is of a broadband configuration, low polarizing effect that is spatially dependent, low scattering, non-absorbing or low absorbing, and is color independent with negligible internal or stray reflections. In contrast to a polarizing beamsplitter where incoming light is reflected at 90 degrees to the path of at least one of the paths of outgoing light such that incoming and all exiting light are basically near normal incident to the faces of the cube, the pellicle beamsplitter in this embodiment overcomes the detrimental design limitations of a typical achromatic beamsplitter. This broadband configuration is necessary because in a typical achromatic beamsplitter it is difficult to successfully achieve very small Fresnel reflections on the surfaces unless the beamsplitter includes coatings that adopt broad wavelength ranges which are very expensive, very sophisticated and difficult to provide.

The pellicle beamsplitter in one embodiment provides better performance than the polarizing beamsplitter in the above described arrangement with the axial camera and reimagers even though a polarizing beamsplitter and ¼ wave plate with axial camera and reimagers would only require the system to lose half of its light once while the pellicle system with axial cameras and reimagers requires the system to lose half of its light twice or successively. This is acceptable due the providing of broadband illumination from the light source which provides more light so extra loss is allowed.

A pellicle beamsplitter is preferred over merely a beamsplitter because the pellicle removes internal obstructions and optical aberrations that are undesirable.

It has been discovered that using the above system, the pellicle beamsplitter is more efficient, provides less stray light, is more spatially uniform, and generally provides better properties than the polarizing beamsplitter when the system uses a broadband light source. The pellicle beamsplitter is all dielectric rather than containing a metallic layer resulting in a beamsplitter that is non-absorbing or low absorbing. The dielectric pellicle beamsplitter is also preferably as close to 50/50 reflective/transmissive. It also preferred that the beamsplitter is low scattering. As a result, the system has optimized the amount of "good" light that passes through while minimizing the amount of "bad" light passing through which is absorbed or scattered light.

Photon motel 131 is critical because 50% of light is lost in the beamsplitter. This large amount of "lost" light needs to be eliminated from the system so an optimized and efficient photon motel is critical. Photon motel 131 is a two walled device where the first wall is a highly efficient light absorbing and controlled reflecting glass surface and the second wall is a highly efficient light absorbing surface optimally positioned to receive the light reflected from the first wall. The first wall is a piece of highly polished absorbing glass that eliminates significant amounts of the light while the remaining light is reflected in a controlled manner but not scattered. In the one embodiment, 96% of the light is absorbed. The reflected light is directed toward the second face which is a flat black coated surface where significant amounts of the light reflected from the first wall is absorbed while the remainder is scattered into a Lambertian distribution. In one embodiment, 90% of the light reflected to the second wall is absorbed while 10% is scattered. The result is that less than ½ of a percent is scattered back into the intermediate focal assembly since 10% of 4% is less than ½ of a percent.

An aluminum anodized mounting holder that is pinned holds the aperture array 132 in place. The pins allow the aperture array to be removed, returned and/or replaced in the exact same position.

Aperture array 132 in the embodiment shown is an opaque pinhole array. Specifically, the aperture array is chrome on glass or chrome on quartz with the chrome being on the first or reflective side while the pinholes are etched out of the second side which is the side facing the sample S (chrome side) while the reflective side faces the beamsplitter. Either one or both sides of the array in one alternative embodiment include an anti-reflective (A/R) coating. The chrome coating has an optical density of 5.

The pinhole array may be of any x by y number of pinholes, while in the most preferred embodiment is an approximately 100 pinhole by an approximately 1000 pinhole array. The holes in this embodiment are of a circular nature although other configurations are contemplated. However, other aperture, pinhole or like arrays of differing numbers and ranges of holes are contemplated.

The aperture array is slightly canted as shown $\beta$ is canting results in the directing or steering away of stray reflections that do not effect the system. For instance, the canting keeps light reflected from the pellicle toward the aperture array that does not pass through a pinhole in the array from being reflected back into the camera reimager and camera. In the embodiment shown the canting $\beta$ is 4.5 degrees although it may be at other angles between 0.1 degree and 25 degrees. As discovered, the greater the cant angle the easier it is to remove stray light such as that caused by the reflection from the chrome surface; however, canting too much introduces other negative effects.

The pinholes in the aperture array are optimized in terms of size and pitch. In one embodiment, the size of the pinholes matches the camera pixels, that is the size of each pinhole matches the diffraction size of the spot coming back from the object imager.

However, in another embodiment, under sampling is used meaning the system has more pinholes than camera pixels, and as such more than one pinhole is mapped or correlated into each pixel. This under sampling reduces the effects of aliasing in the system so that holes do not have to match up directly with the pixels and thus alignment, distortions, and imperfections in optical system and other similar issues are avoided because this design assures that the same or substantially the same amount of light reaches each pixel regardless of the orientation, phase, etc. of the pixel with respect to a pinhole. The under sampling also broadens the depth response profile of our optical system to allow the system to operate over a broad range of three dimensional heights on the sample S.

In addition, in one embodiment the apertures are orthogonal or grid-like. However, in alternative embodiments the apertures are non-orthogonal or non-grid-like such as a hexagonal or other geometric pattern. This non-orthogonal pattern in at least certain applications may reduce aliasing and alignment issues.

Figure 2:
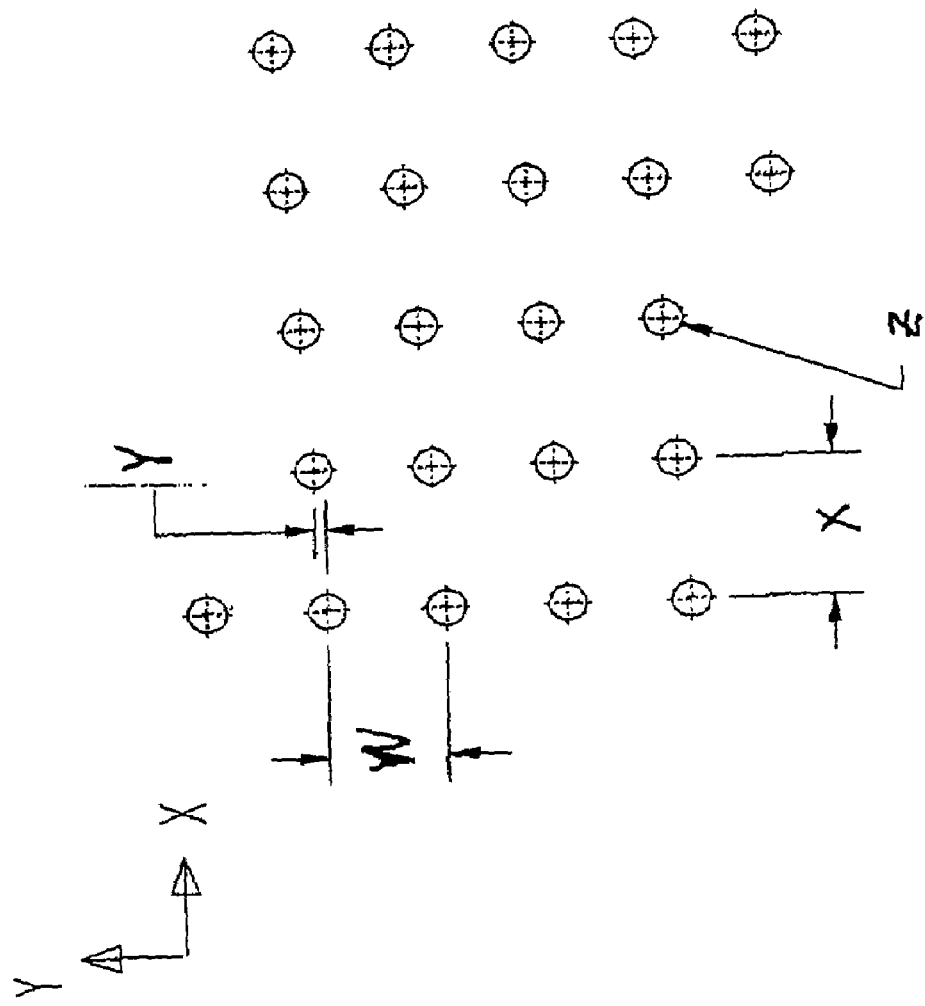
FIG. 2 is a drawing of the aperture array of the present invention.

In a more preferred embodiment, the apertures are in a unique "rhombus-like" pattern as is shown in FIG. 2 which reduces diffraction problems and cross talk when coupled with a line scan camera such as a TDI line scan camera. In this pattern, the pinholes in the y direction define an axial line in alignment with the y axis, while the pinholes in the x direction are sheared, angled or offset in relation to the x axis. In addition in certain embodiments, the distance between pinholes in the x direction differs from the distance between pinholes in the y direction.

This unique pattern of not aligning the pinholes in both x and y directions at ninety degrees to each other reduces or eliminates the cross talk as well as allows larger diameter pinholes without losing resolution. Rotational alignment issues are also reduced or eliminated between the camera and aperture array when this pattern is used coupled with a TDI camera. The field of view at the camera is also more uniform because the apertures do not fall one for one on a pixel and instead overlap the pixels slightly and be integrating all of the columns allow equalizing effect and aliasing is reduced or eliminated.

FIG. 2 shows one specific design for the aperture array. The array has an x axis and a y axis as shown. The distance between each pinhole in the y direction is shown as W microns, and the distance between each pinhole in the x direction is shown as X microns, although each may be of a different distance. The holes align in the y direction along the y axis, while the holes in the x direction do not align in the x direction along the x axis and instead run diagonally as shown whereby the offset from the center of each pinhole in the x direction is shown as Y microns although it may be a different amount. It is also preferred that the diameter of each pinhole be Z microns, although other diameters are acceptable.

In one embodiment, the diameter of each pinhole is Z and is preferably 16 $\mu$m, the distance between each pinhole in the x direction is X and is preferably 63 $\mu$m, the distance between each pinhole in the y direction is W and is preferably 51 $\mu$m, and the offset from the x axis of each pinhole in the x direction is y and is preferably 5 $\mu$m. The ratio of the diameter of a pinhole to its distance from another pinhole in the x direction and the y direction, and the offset are critical to eliminate diffraction and cross talk.

Pitch is preferably calculated from pinhole size which is optimized to numerical aperture size. The pinhole size is chosen inter alia to match the diffraction of the object imager. The pitch is twice the pinhole size which optimizes the reduction of cross talk between pinholes while maximizing the number of resolution elements. Magnification and spatial coverage may then be adjusted to optimize resolution at the wafer surface.

Another key feature of this invention is that light passing from the aperture array is in transmission so that any surface anomalies on the pellicle beamsplitter are irrelevant to the imaging properties of our system and we are not susceptible to vibrations of pellicle beamsplitter.

The positioning of the aperture array into the system provides a confocal response. Only light that passes through an aperture in the aperture array, passes through the dual telecentric object imager, reflects off of the sample S, passes back through the dual telecentric object imager, and passes back through an aperture in the aperture array is in focus. This confocal principle results in bright illumination of a feature in focus while dim or no illumination of an out of focus feature.

Aperture array in the preferred embodiment is a fused-silica material such as chrome on glass or chrome on quartz because of the low coefficient of thermal expansion. It may alternatively be made of any other material having a low coefficient of thermal expansion such as air apertures, black materials, etc. This eliminates a mismatch potential between pixel sizes and the CCD camera elements.

The object imager 134 in the preferred embodiment shown is of a dual telecentric design. The object imager includes a plurality of lenses separated by one or more stops or baffles. In one embodiment, the object imager includes two to six lenses, and preferably three to four, on the right side of the imager and two to six lenses, and preferably three to four, on the left side of the imager separated in the middle by the stop. Since the imager is dual telecentric, the stop is located one group focal length away from the cumulative location of the lenses on each side.

The object imager functions to: (1) provide a front path for the light or illumination to pass from the aperture array to the object (wafer or sample S), and (2) provide a back path for the reimaging of the object (wafer or other sample S) to the aperture array 132.

This system is unique because it is a dual telecentric optical imager/reimager. This dual telecentric property means that when viewed from both ends the pupil is at infinity and that the chief rays across the entire field of view are all parallel to the optical axis. This provides two major benefits. One benefit which relates to the object or sample end of the imager is that magnification across the field remains constant as the objectives focus in and out in relation to the sample. The second benefit relates to the aperture end of the imager where the light that comes through the aperture array is collected efficiently as the telecentric object imager aligns with the telecentric camera reimager.

The optical throughput is very high. This is a result of a numerical aperture of the system on the object side is in excess of 0.23 with a field of view on the object with a diameter of 5 mm.

In an alternative embodiment, the numerical aperture of the object imager may be adjustable or changeable by placing a mechanized iris in for the stop. This would allow for different depth response profile widths. This allows for broader ranges of bump or three dimensional measurements since the taller the object that it is, desirable to measure the lower the desirable numerical aperture to maintain speed of the system. Similarly the smaller the object to be measured, the more desirable it is to have a higher numerical aperture to maintain sharpness, i.e., accuracy.

The magnifications of the object imager are 4×. The aperture array is four times larger than the object (sample S).

The camera reimager 136 in the preferred embodiment shown is of a telecentric design, although it may in other embodiments be a dual telecentric design. The camera reimager includes a plurality of lenses separated by a stop. In one embodiment, the camera reimager includes two to six lenses, and preferably three to four, on the right side of the reimager and two to six lenses, and preferably three to four, on the left side of the reimager separated in the middle by the stop. Since the reimager is telecentric, on the telecentric side which is the side nearest the pellicle beamsplitter, the stop is located one group focal length away from the cumulative location of the lenses on that side.

The camera reimager functions to provide a path for the light passing through the aperture array from the object imager to the camera. It is preferable to match or optimize the camera reimager properties to the object imager and the camera where such properties include numerical aperture, magnifications, pixel sizes, fields of view, etc.

The telecentric properties of the camera reimager are on the aperture array side or end so that it efficiently and uniformly across the field of view couples the light coming through the aperture array from the object imager 134. It is pixel sampling resolution limited so its aberrations are less than that from the degradation of the pixel sampling. Its numerical aperture is designed based upon the object imager so any misalignments between the reimagers do not translate into a field dependent change in efficiency across the field of view.

The combined system magnification of the object and camera imagers/reimagers is chosen to match spatial resolution at the object to pixel size.

The magnifications of the camera reimager are 0.65×. The CCD or detector array is 0.65 times the aperture array. Thus, the preferred object and camera reimager magnification is 2.6×.

The imagers/reimagers have very high numerical apertures, and the greater the numerical aperture the finer the resolution and the sharper/narrower the depth response curve.

In addition, an optional feature in this invention that is used in certain embodiments is the canting of either the sample S with reference to the optical axis of the entire optical subsystem, or vice versa (that is the canting of the entire optical subsystem with respect to the sample S). This option compensates for the canting of the aperture array as described above thus maintaining the Scheimpflug condition. In the Figure, the canting is shown as a. In the current preferred embodiment, the cant angle a is 0 degrees, although in other embodiments it ranges from 0 to 5 degrees such as a cant angle a of 1.2 degrees in one alternative embodiment.

It is also an option not to cant the sample or the optical subsystem when the aperture array is canted. In this scenario, some desensitivity of the signal occurs but is often not significant or noteworthy.

The camera 126 may be any line scan camera, area scan camera, combination of multiple line scan cameras, time delay integration (TDI) line scan camera or other camera or cameras as one of skill in the art would recognize as functionally operational herewith. The camera may be angled γ.

In the embodiment shown in the Figures, the camera 126 is a TDI camera. TDI provides additional speed by transferring the charge such that the system integrates light over time. The aperture array with line scan camera uses only one array of pinholes while with TDI the aperture array is 100 or more arrays by multiple apertures in each line (an example is 100 lines by 1024 apertures per line).

Image acquisition is typically limited by camera read rates, stage velocity and light. This broadband solution eliminates or significantly reduces light issues. Thus continue scalability of the system will occur as read rates continue to improve for TDI cameras or related technology such as CMOS imagers. Alternatively, system throughput is also increasable by increasing the number of apertures from approximately 1000 to 2000 or even 4000.

Sampling or viewing may be 1:1 or at another ratio. Where at 1:1, the camera operates at a 1 pinhole to 1 pixel ratio. Where under sampling is used, the camera is at a ratio other that 1:1 pinholes to pixels, and in one embodiment is at 1½ or 2 pinholes per pixel element at the camera sensor.

Light passes through the system as follows: Light source 122 illuminates and directs such light toward beamsplitter 130. Some of the light that reaches the beamsplitter passes through the beamsplitter and emanates out of the entire system thus avoiding interference with the system, a small amount is lost within the beamsplitter, and the remaining light is reflected toward the aperture array. Light that reaches the aperture array either passes through an aperture therein, or hits the plate around the holes in the aperture array and is reflected out of the system due to the cant. Light that passed through the aperture array is reimaged and collimated in the dual telecentric object imager. The light is directed toward the sample S and reflects off of the sample S. If the point that is illuminated is in or near focus, substantially all of the light reflects back into the object imager while if not in focus then little or none is reflected back. Light passes back through the object imager and is directed toward the aperture array. Light that reaches the aperture array either passes through an aperture therein, or hits the plate around the holes in the aperture array and is reflected out of the system due to the cant. Light that passed through the aperture array is in focus due to the confocal principle, and it is reimaged and collimated in the telecentric camera reimager. It is directed into the camera and the intensity recorded. In any given pass, the above process occurs for every point on the sample that is being viewed.

The light that passes through the system is received by camera 126 and stored. After this process has been repeated at different heights, and across at least a portion of the surface, all of the stored data is then processed by a computer or the like to calculate or determine the topography of the sample including the location, size, shape, contour, roughness, and/or metrology of the bumps or other three dimensional features thereon.

In one of the current design and embodiment for bumps or other three dimensional features, the process involves one, two or more (generally three or more) passes over all or a selected portion of the sample surface S each at a different surface target elevation to measure surface elevation followed by two or more (generally three or more) passes each at a different bump target elevations to measure bump elevation followed by calculations to determine bump height. The result of the passes is an intensity measurement for each point at each elevation where these points as to surface elevation and separately as to bump elevation are plotted or fitted to a Gaussian curve to determine the elevation of both the surface and the bump from which the actual bump height at a given point is determined. It is the difference between the surface elevation and the bump elevation.

In more detail, a pass is made over a portion or the entire surface of the sample S. Intensity is determined for each pixel. Initially, a course or approximate surface elevation is used that is approximating the surface location or elevation of the sample S. The entire sample (or portion it is desired to measure) is scanned and the intensities are noted for each pixel, while if very small or no intensity at a given point then the system is significantly out of focus at that location or pixel (an example is scanning at the surface elevation where bumps exists results in little or no intensity feedback). This step is generally repeated twice more (though any number of passes may be used so long as a curve can be calculated from the number of passes) at a slightly different elevation such as 5, 10 or 20 microns difference in elevation to the first pass. The result is three data points of intensity for each pixel to plot or fit a Gaussian curve to determine the actual wafer surface elevation at that location. The wafer surface elevation is now known for the entire sample except where bumps or other significant three dimensional protrusions or valleys exist since each of these reported no intensity as they were too out of focus to reflect back any light. Curve fitting may be used to determine surface location under the bumps.

The second step is to determine the elevation of these significant protrusions or valleys (such as bumps). Another pass is made over a portion or the entire surface of the sample S (often only where bumps are expected, known, or no intensity was found in the surface elevation passes). This pass occurs at a course or rough approximation as to the elevation of the expected bumps such as 50, 100, 200, 300 or the like microns above the surface. Intensity is determined at each pixel as the entire sample (or only select locations where bumps are expected, known or no intensity was previously found) is scanned and the intensities are noted for each pixel, while if very small or no intensity at a given point then the system is significantly out of focus at that location or pixel (an example is scanning at bump elevations where no bump exists results in little or no intensity feedback). This step is generally repeated several more times (though any number of passes may be used so long as a curve can be calculated from the number of passes) at a slightly different elevation such as 5, 10 or 20 microns different. The result is multiple data points of intensity for each pixel to plot or fit a Gaussian curve to determine the bump elevation at that point.

Once the surface elevations are known and the bump elevations are known, the bump heights can be determined. The surface elevations are determined for the bump location based upon analysis, plotting, and/or other known curve extension techniques of all of the proximate surface elevations around the bump. The difference between a bump elevation and the proximate surface elevations therearound, or the bump elevation and the calculated surface elevation thereunder, equate to the bump height for a given bump.

In sum, the scanning process for the above invention is as follows: The system will scan lines across the sample surface S at a fixed elevation above the sample surface S. This scan will generate one z axis elevation on a depth response curve for each pixel on the sample under the scan. The sensor will then be moved in the z axis direction to a second elevation and the scan will be repeated to generate a second z axis elevation on the depth response curve for each location on the sample S under the scan. This can then be repeated any number of times desired for the interpolation method used (typically at least two or three scans, although more are certainly contemplated and will improve accuracy). The multiple locations on the depth response curve are then interpolated for each pixel to generate a map of the surface height under the scan. The elevation of the sample surface S is now known.

In the case of significant three dimensional protrusions (such as bumps), this process may be repeated at the approximate elevation of the outermost portion of the protrusions just as it was performed above at the approximate elevation of the sample surface S. The bump elevations will then be known, and the bump heights are then calculated as the difference between the surface elevation and the bump elevation.

It is important to understand that the size of the "in focus" region is determined by the telecentric imaging lens. If this lens has a larger numerical aperture (~ratio of the focal length to diameter) the focus range will be small, and conversely if the lens has a low numerical aperture the focus range will be large. The best in focus range is dependent on the elevation range that needs to be measured.

The invention also in at least one embodiment is capable of adjusting depth response. This is desirous since with larger bumps a broader depth response is desirable while with smaller bumps a thinner or smaller depth response is desired. In effect, the system degrades the high numerical aperture to look at larger or taller bumps, and this assists in maintaining speed. Inversely, to view smaller or thinner bumps it is desirable to provide a higher numerical aperture. This broadening of depth response is accomplished either by providing a baffle to adjust the aperture, or by providing or increasing the tilt of the sensor.

A significantly different alternative involves imaging multiple heights at each point rather than making multiple passes. This is accomplished by using multi-line line scan cameras where each camera or sensor is looking at different elevations. For example, a four line, line-scan camera system would involve line 1 reading elevation 0, line 2 reading elevation plus 20 microns, line 3 reading elevation plus 40 microns, and line 4 reading elevation plus 60 microns. All four data points in this example are gathered simultaneously. It is also contemplated and recognized that a CMOS imager would work successfully. Alternatively, multiple TDI sensors could also be used stacked close together. It is necessary to introduce a variable amount of optical path difference between each scan lines either by shifting the aperture array or introducing a difference in compensator thickness in a media such as glass between the aperture arrays which are in a plane and the end of the object imager closest to the aperture array. The result is multiple separate planes that are conjugated to separate z heights at the wafer or sample surface S. In this case where imaging occurred as to multiple heights on a given pass, the surface height calculation and the bump height calculation will involve only one pass each.

In yet another alternative embodiment, two modes of speed are provided. A precise mode is provided where scanning occurs as to every die in either or both surface elevation determination and bump elevation determination. A faster mode is provided where scanning as to wafer surface elevation is performed only in one or a few places along the wafer and interpolation is used to calculate the surface over the remaining surface including at the die.

Some alternative light sources include an illuminator with a filament designed for providing a uniformly filled area internally imaged first into a numerical aperture stop and then reimaged into the telecentric pupil of the object imager and whereby the angular spectrum from the filament is mapped first into a field stop inside the illuminator and then reimaged to the a filed located in the intermediate focus or IFA of the object imager at the aperture array. Another light source is an illuminator with a filament designed to provide a uniformly filled area that is imaged into the telecentric pupil of the imaging system (object imager) and whereby the angular spectrum from the filament is mapped into the field located in the intermediate focus or IFA of the imaging system at the aperture array and whereby the light outside the useful $A\Omega$ product of the imaging system is eliminated via a series of baffles. Yet another light source is an illuminator with an array of bright monochromatic or quasi-monochromatic sources instead of a filament. Yet an even further illuminator is a bright monochromatic or quasi-chromatic source that is collimated and directed into the field located in the intermediate focus or IFA of the imaging system at the aperture array whereby preferably an array of lenslettes are employed to create an angular spectrum at each aperture, whereby it is preferably but optional that the source is apodized.

Accordingly, the invention as described above and understood by one of skill in the art is simplified, provides an effective, safe, inexpensive, and efficient device, system and process which achieves all the enumerated objectives, provides for eliminating difficulties encountered with prior devices, systems and processes, and solves problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the invention's description and illustration is by way of example, and the invention's scope is not limited to the exact details shown or described.

Having now described the features, discoveries and principles of the invention, the manner in which it is constructed and used, the characteristics of the construction, and the advantageous, new and useful results obtained; the new and useful structures, devices, elements, arrangements, parts and combinations, are set forth in the appended claims.

What is claimed is:

1. An inspection device comprising:
   a light source;
   a pellicle beamsplitter for receiving light from the light source and redirecting said light;
   an aperture array for receiving light from the pellicle beamsplitter wherein the aperture array is a two dimensional array of pinholes having an x axis and a y axis ninety degrees apart, and wherein the x direction defines a scan line direction and the distance between pinholes in the x direction is greater than the distance between pinholes in the y direction; and
   an imaging system including an object imager including a plurality of lenses, a camera reimager including a plurality of lenses, and a camera for acquiring an image;
   wherein the pinholes in the y axis direction are axial to the y axis, while the pinholes in the x axis direction are not axial to the x axis.

2. The inspection device of claim 1 wherein the pinholes are in a rhombus pattern.

3. The inspection device of claim 2 wherein the pinholes in the x axis direction are offset from adjacent pinholes.

4. The inspection device of claim 3 wherein the offset is approximately 5 microns.

5. The inspection device of claim 4 wherein the pinholes in the y direction are approximately 51 microns apart, while the pinholes in the x direction are approximately 63 microns apart.

6. The inspection device of claim 5 wherein the diameter of each pinhole is approximately 16 microns.

7. The inspection device of claim 1, wherein the aperture array is stationary.

8. The inspection device of claim 1, wherein at least one of the object imager and/or camera re-imager is a dual telecentric type imager and/or re-imager.

9. The inspection device of claim 1, wherein the pinholes are arranged in a non-radial pattern.

10. The inspection device of claim 1, wherein the aperture array has at least one non-reflective major surface.

11. The inspection device of claim 1, wherein a size of each of the pinholes is selected to match a diffraction of the object imager.

12. The inspection device of claim 1, wherein the aperture array is canted to be non-perpendicular to a focal axis of the object imager.

* * * * *